United States Patent [19]

Farris

[11] 4,067,692
[45] Jan. 10, 1978

[54] ODOR CONTROL DEVICE

[76] Inventor: Richard W. Farris, 1508 Indiana Ave., La Porte, Ind. 46350

[21] Appl. No.: 694,540

[22] Filed: June 10, 1976

[51] Int. Cl.$^2$ .......................... A61L 3/02; A61L 9/01; A61L 9/04; F24F 3/12

[52] U.S. Cl. .................................... 21/74 R; 21/104; 21/122; 98/40 VT; 239/59; 239/75; 261/39 R; 261/DIG. 65

[58] Field of Search ................. 21/53, 55, 74 R, 75, 21/104, 121–127; 239/75, 56, 57, 59; 236/44 R, 49, 93 R; 98/40 VT; 126/113; 261/39 R, DIG. 65, DIG. 15

[56] References Cited

U.S. PATENT DOCUMENTS

| | | | |
|---|---|---|---|
| 2,708,595 | 5/1955 | Ludwig | 239/57 |
| 3,442,602 | 5/1969 | Diehl | 21/74 R |
| 3,464,400 | 9/1969 | Wellman | 126/113 |
| 3,661,323 | 5/1972 | Farris | 21/74 R |

Primary Examiner—Morris O. Wolk
Assistant Examiner—Bradley R. Garris
Attorney, Agent, or Firm—Marmaduke A. Hobbs

[57] ABSTRACT

An odor control device for use with an air passage of a main heating and/or air conditioning system having a blower. The device has a body with an air flow chamber therein, a panel secured to the body and having an air inlet port for admitting air into the chamber, a rotatable plate mounted on the panel, and a container for odor conditioning material mounted on the rotatable plate and preferably held thereon by a magnetic bar attached to the plate and attracting a perforated metal plate in the container, thereby permitting the container to be easily removed from the plate and attached thereto. The panel and plates have communicating arcuate inlet and outlet passages to permit the air to pass from the chamber in the body to the container and thence to the conduit of the main system. The panel contains a main air intake port for the device, and an opening is provided in the body for communicating directly with the main system conduit, and thermostatically controlled shutters control the intake and last mentioned opening.

11 Claims, 11 Drawing Figures

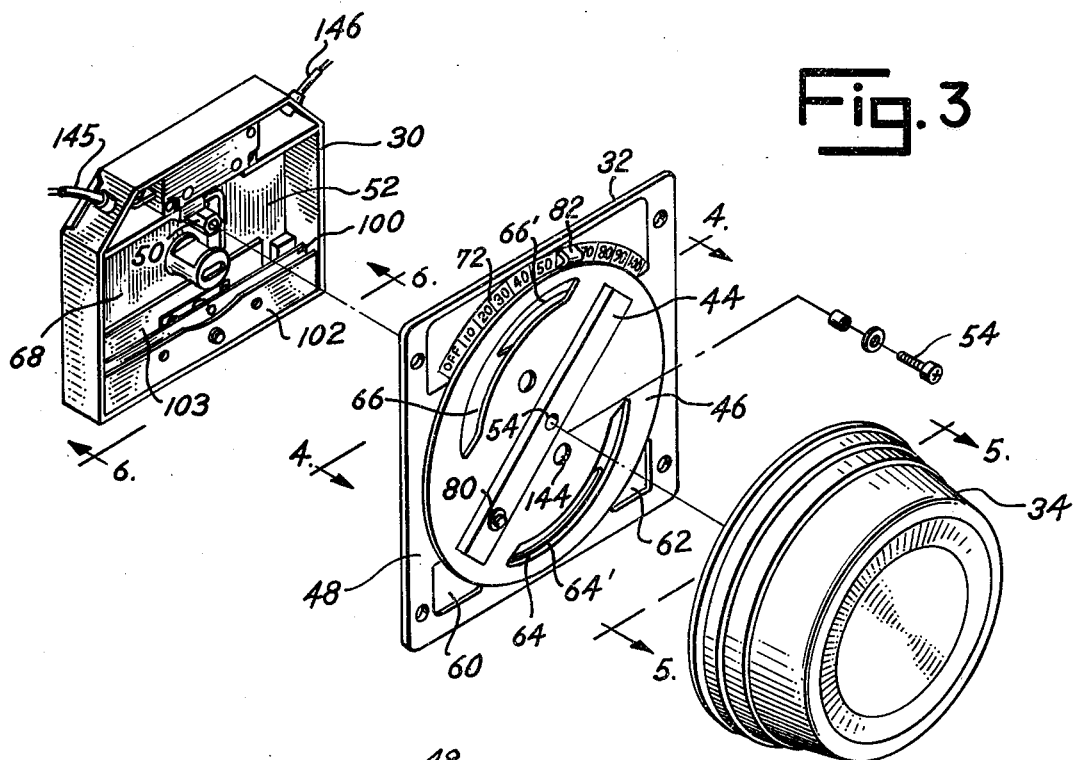
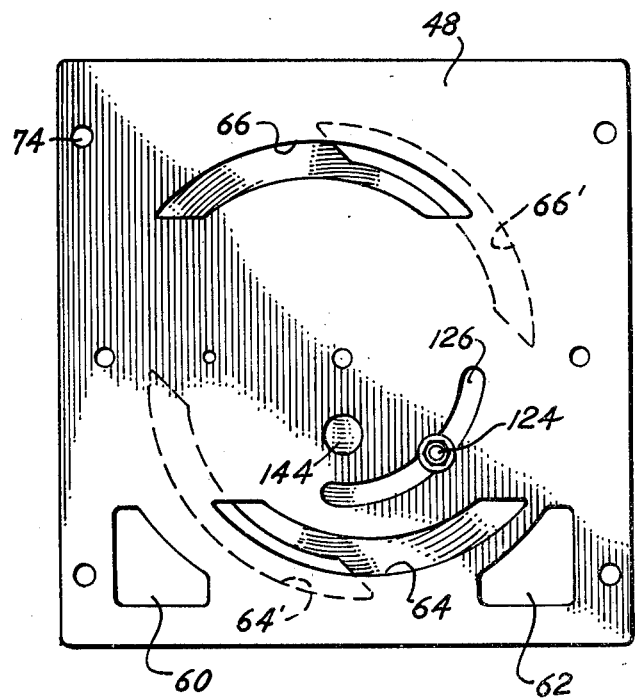
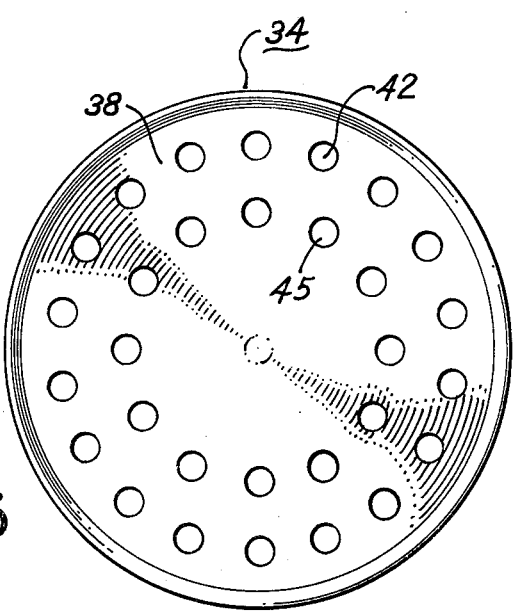

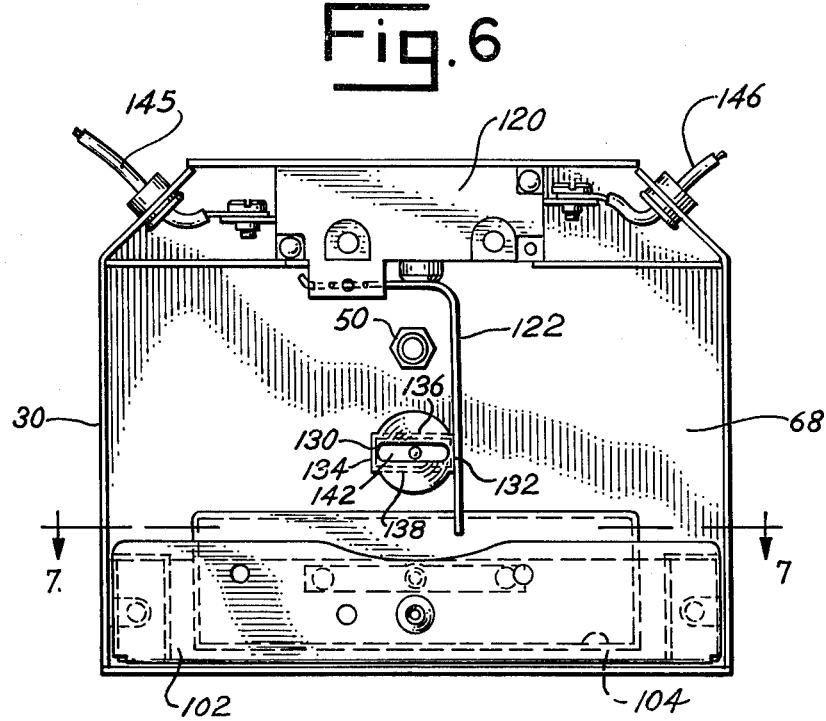
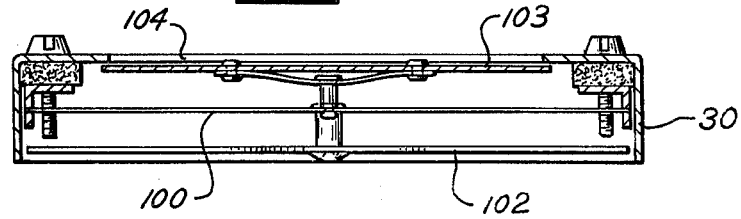

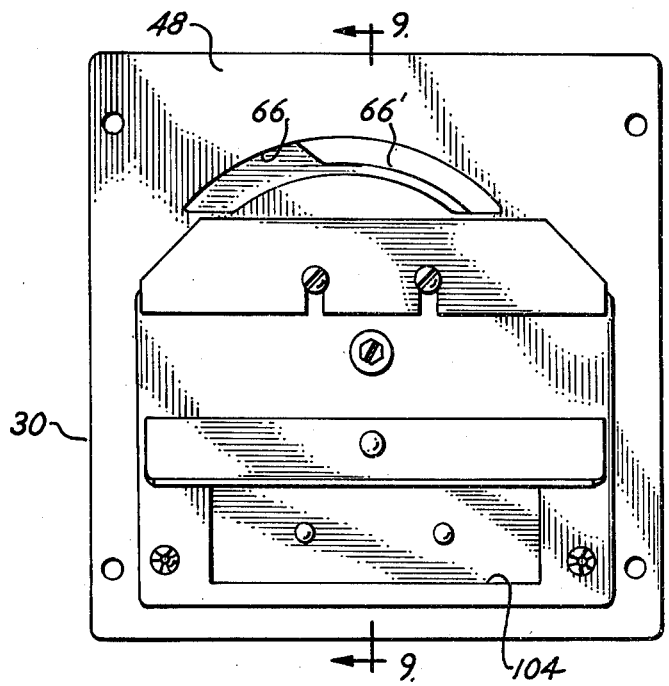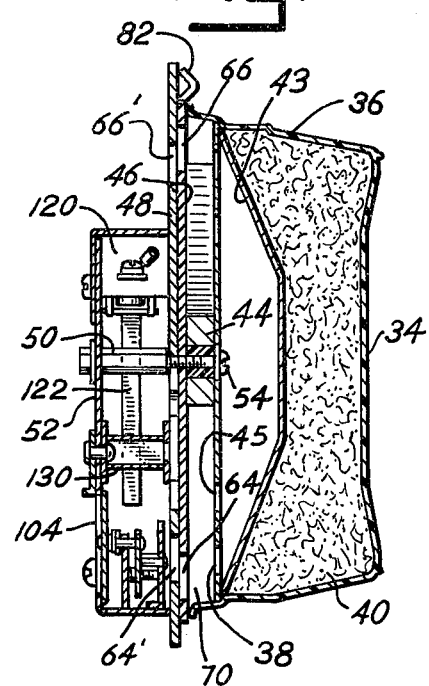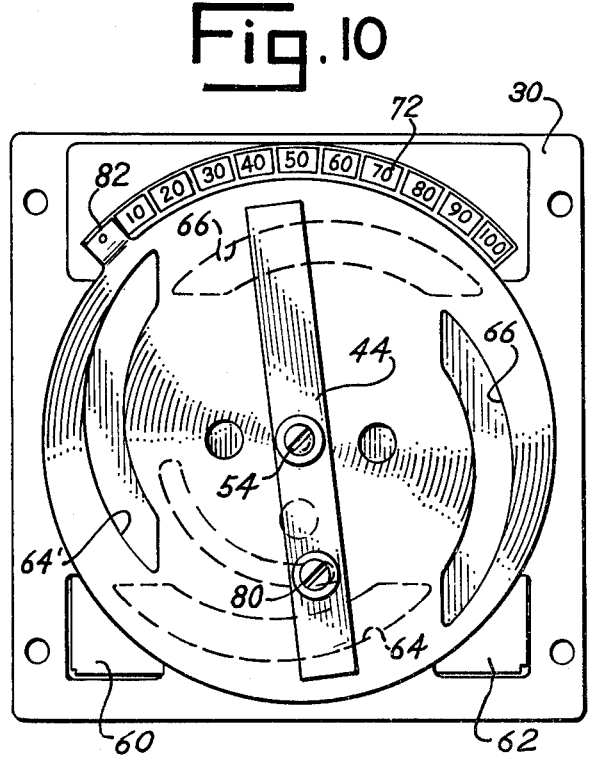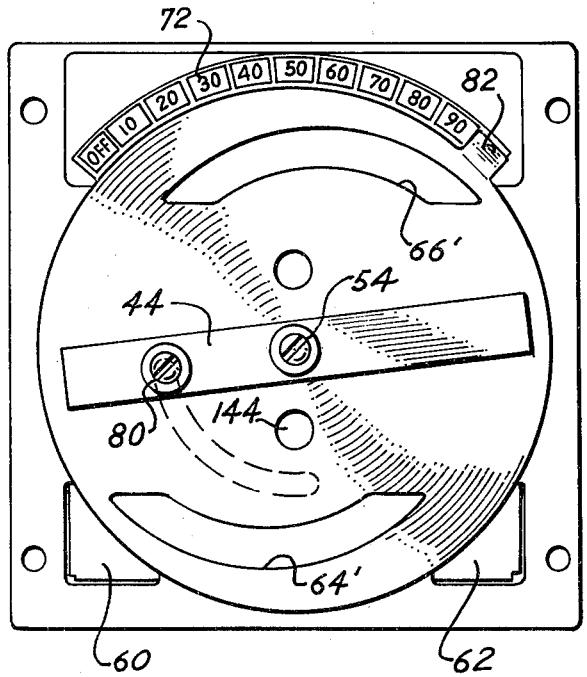

ODOR CONTROL DEVICE

Today, the modern dwelling is equipped to contend with the preponderance of nature's assorted discomforts, i.e. cold, heat, humidity, pollen, dust and smoke. All can be effectively controlled. Conspicuous by its absence from this impressive array is the ability efficiently and specifically to control unpleasant odor. Contemporary tight and heavily insulated construction, largely an accommodation for modern indoor comfort components, insures that any odor originating inside will remain inside and be distributed throughout the structure by the indoor comfort equipment. Various methods for specifically controlling indoor odors have existed for some years. Their practicality is, however, questionable. One increases indoor air contamination and the load on the central system. Another cannot be turned off and requires rather difficult and expensive element replacement, and some are limited to area use and are not applicable to central systems. All are relatively inefficient and costly to operate.

The foregoing disadvantages have been effectively overcome by devices invented by the applicant, and one such device is covered by applicant's U.S. Pat. No. 3,661,323 issued May 9, 1972, relating to an odor neutralizing device. The odor neutralizing device disclosed in the foregoing patent accomplished the objective of neutralizing the odor, and was so constructed and designed that it could be installed either on a new or existing heating and air conditioning system without making any substantial changes in the basic system, or requiring any motors, blowers or fans in addition to those of the original heating and air conditioning system. The present odor control device is an improvement on the applicant's prior odor neutralizing device and provides, in addition to the foregoing objects, a self contained and compact odor neutralizing device which can be mounted on and connected directly into the return air duct, either on the side or bottom thereof, and which can readily and conveniently be serviced and regulated without rendering the basic heating system and/or air conditioning equipment temporarily inoperable.

Another object of the present invention is to provide full and uniform odor control throughout the entire dwelling or other structure in which the equipment is installed, and which, while being used in conjunction with the heating and/or air conditioning equipment, can be operated regardless of whether the equipment is being used to heat or cool, and can be controlled independently of the controls of the basic equipment in which the device is installed.

Still another object of the invention is to provide a device of the aforesaid type which may be adjusted to vary the intensity levels over a wide range, and which will maintain the selected level within narrow limits, and which utilizes a solid or semi-solid chemical for performing the odor control action and maintains a near constant evaporation rate, regardless of the level or amount of the neutralizer in the device or the temperature of the air passing therethrough.

Further objects and advantages of the invention will become apparent from the following description and accompanying drawings wherein:

FIG. 3 is an exploded, perspective view of the principal parts or subassemblies of the odor control device shown in the preceding figures;

FIG. 4 is an elevational view of one of the subassemblies shown in FIG. 3, the view being taken from line 4 — 4 of FIG. 3;

FIG. 5 is an elevational view of another of the subassemblies shown in FIG. 3, the view being taken from line 5 — 5 of FIG. 3;

FIG. 6 is an elevational view of the body of the control device shown in FIG. 3, the view being taken from line 6 — 6 of FIG. 3;

FIG. 7 is a horizontal cross sectional view of the body shown in FIG. 3, the section being taken on line 7 — 7 of FIG. 6;

FIG. 8 is a rear elevational view of the body of the odor control device shown in the preceding figures;

FIG. 9 is a cross sectonal view taken on line 9 — 9 of FIG. 8; and

FIGS. 10 and 11 are front elevational views of the intermediate subassembly shown in FIG. 3, illustrating the operation of this assembly showing two different operating positions thereof.

Figure 1:
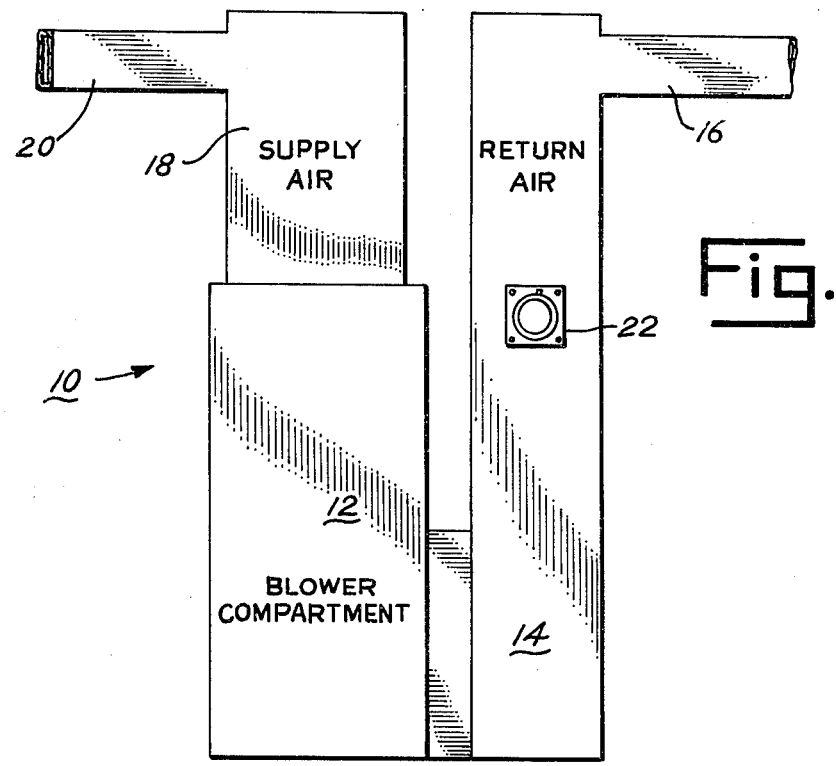
FIG. 1 is a side elevational view of a furnace and/or air conditioning system for a home, business or the like, showing the odor control device mounted thereon.
Figure 2:
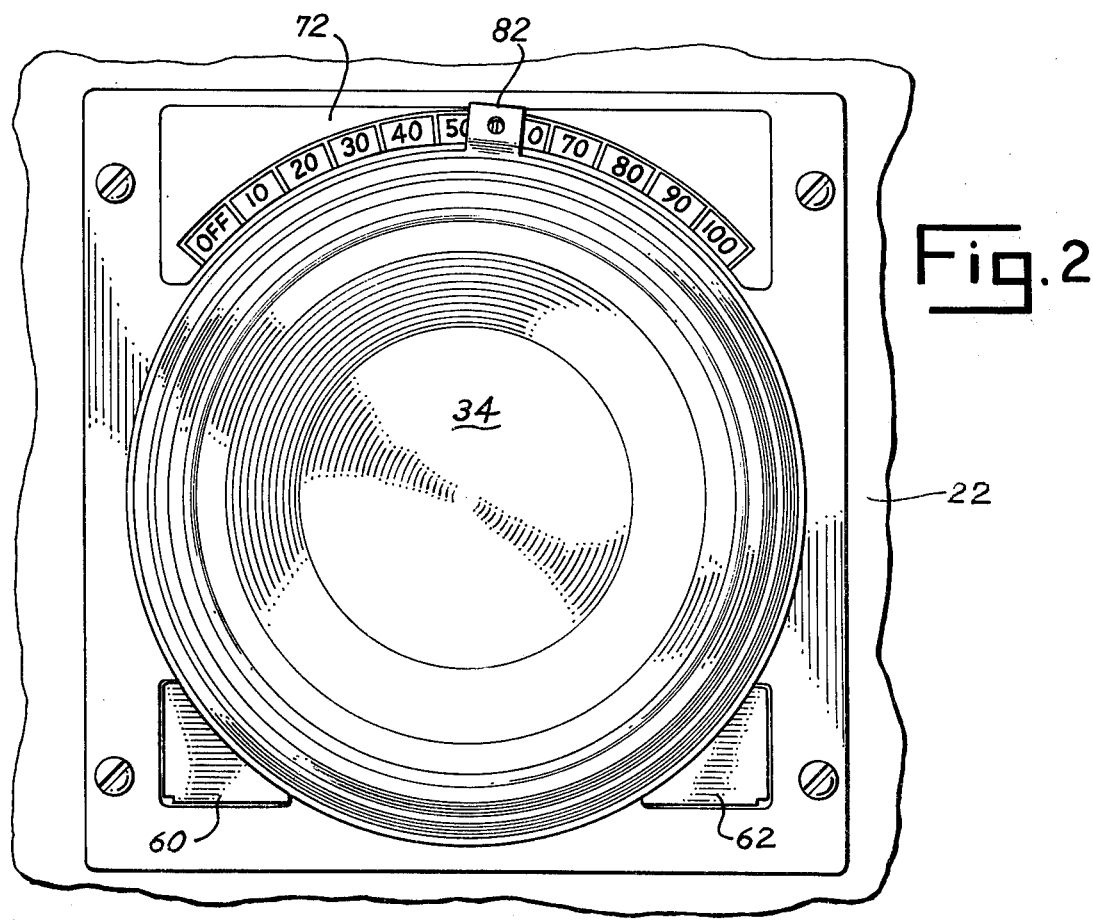
FIG. 2 is a front elevational view of the odor control device.

Referring more specifically to the drawings and to FIG. 1 in particular, numeral 10 indicates a furnace and/or air conditioner having a blower compartment 12, return air conduits 14 and 16, bonnet 18 and warm or cooled air duct 20. The system shown would normally consist of a heating and/or cooling unit, and air supply conduits operating in conjunction with the system regardless of the mode. The blower in compartment 12, which may be considered conventional for the purpose of the present description, draws air through duct 16 and conduit 14, and discharges it into a compartment or compartments in which the heating and/or cooling elements are located, and thence forces the air through bonnet 18 and duct 20 to the space to be heated or cooled.

The present odor control device 22 is shown mounted on the air return conduit 14, where the chemical neutralizer or deodorizer in the device is mixed with the air passing through the return conduit to the blower compartment. The device may be located in various positions, on the blower compartment 12, or on either the vertically or horizontally disposed sides of the conduits or ducts, such as conduit 14 or duct 16. In the event it is mounted on a horizonal duct, it may be placed on the top or bottom sides in a horizontal position or on either of the two sides in vertical position. The device will operate effectively regardless of the position in which it is placed.

The odor neutralizing device 22 shown in the drawings includes a body 30, a control assembly 32, and a container 34 in which the odor neutralizing material is disposed. The container consists of a plastic cup-shaped member 36 having a perforated metal partition plate 38 and the odor neutralizing material 40 disposed in the container. An outer series of annularly arranged holes 42 and an inner series of annularly arranged holes 45 permit air to pass through the metal plate and through a porous element 43 where the air mixes with the odor neutralizing material. The container is removably held to the control unit 32 by a bar magnet 44 secured to a rotatable plate 46 on a rectangular stationary plate or panel 48.

In the embodiment of the invention illustrated in the drawings, body 30, which is constructed of metal and is rectangular in shape, has a stem 50 secured to back 52 for supporting plate 48 by the use of a screw 54 extending through magnet 44 and the rotatable and rectangular plates. Plate 48 contains air inlet ports 60 and 62 and air inlet passage 64 and air outlet passage 66. The inlet ports 60 and 62 admit air into chamber 68 of body 30 and thence through passages 64 and 64' in the two plates which direct the air into space 70 and thence through holes 42 and 45 of the plate 38. The air then passes along porous layer 43 and mixes with the odor neutralizing material and then passes through passages 66 and 66' into the duct where it mixes with the air flowing therein. The passages 64 and 64' are arcuate in shape and are so arranged and designed with respect to each other that the actual effective passage is small when the device is operating in a low range, and passages 66 and 66' likewise are arranged and designed to provide a low air flow under the same conditions, and all four passages provide a high air flow when the device is operating somewhere near maximum capacity. The two sets of arcuate slots forming the four passages progressively increase and decrease with movement of the setting on the device between low output and high output. However, the rotation of the plate is linear so that any increment of dial 72 results in a substantially linear adjustment in air flow through the four passages 64 and 64' and 66 and 66'. The passages 66 and 66' discharge the air directly into the air conduit or duct, and the device is rigidly retained in operating position on the duct by screws or other securing means through holes 74 around the periphery of plate 48. A screw or boss 80 on magnet 44 extends into one of holes 45 so that rotation of container 34 rotates plate 46 while the container is held in operating position on the plate by the magnet. A hand 82 attached to plate 46 is used in conjunction with dial 72 to indicate the setting of the openings in plate 46 with dial 72 to indicate the setting of the openings in plate 46 with respect ot the openings in plate 48.

In order to compensate for the increased volatility of the odor neutralizing composition, and hence the concentration of the composition in the air discharged from the device as the temperature increases, a temperature compensating means is included in the device. This consists of the thermostatic element 100 rigidly held at each end and carrying two moveable plates or shutters 102 and 103. The shutter 102 controls the air flow through ports 60 and 62, while shutter 103 controls air flow through opening 104 in back 52. When the temperature of the air increases, the thermostat flexes forwardly, thus moving shutters 102 and 103 forwardly as viewed in FIGS. 3 and 9, thereby restricting the air flow through ports 60 and 62 and simultaneously permitting increased air flow from chamber 68 through port opening 104. In the movement of the shutters forwardly with an increase in the air temperature, the air flow into the device is not only restricted but the air flow from the device by-passing the neutralizing material is likewise increased, permitting air to flow directly into the air duct rather than passing through passages 64 and 66 where the air would absorb the neutralizing vapors. When the temperature is relatively low, the thermostatic element moves the two shutters to the rear, thus increasing the air flow through ports 60 and 62 and decreasing the air flow directly from chamber 68 through opening 104. The thermostat continuously varies the position of the two shutters in accordance with the variations in temperature of the air passing through the device.

Since the blower or fan on the main heating or air conditioning system must be on in order for the present device to be operable, and since there may be times when there would be no demand for either heating or cooling but yet a need for deodorizing, a control switch 120 is incorporated in the unit for turning the blower on and off as the present device is made operable or inoperable, when the main system is not otherwise operating. Switch 120, which is of the micro-switch type, is mounted in the upper part of body 30 and has an operating arm 122 extending down into the chamber 68. This arm for controlling the switch is operated by a stem 124 secured to rotating plate 46 and extending through slot 126 in plate 48 and engaging the left hand side of arm 122, as viewed in FIG. 6. When the hand on the dial is moved to "off" position, stem 124 engages arm 122 and moves it in a counterclockwise direction to turn off the switch and thus render the fan inoperable if it is not otherwise being operated through the standard conrols for the system. In some instances, it may be desirable not to have the main air system controlled by switch 120. This is accomplished by member 130 having facets 132 and 134 for holding arm 122 in position to turn off the switch, and facets 136 and 138 for permitting the arm to swing in clockwise direction and thereby permit the switch to close and operate the air conditioning system. The rotating member 130 is manually set by the use of a screw driver in slot 142 inserted through a pair of openings 144 in plates 46 and 48 when the dial is in full capacity position. The electrical connection to the main system through the micro-switch is through lead wires 145 and 146.

In the operation of the present odor control device, with the device mounted on an air return conduit or duct such as illustrated in FIG. 1, the rotation of container 34 rotates plate 46 and hand 82 to the position to obtain the desired odor neutralizing component content in the air of the living space. The air then flows through ports 60 and 62 into chamber 68, and thence through ports 64 and 64' and through holes 42 and 45 where it absorbs the vapors from the effective neutralizing material. The air is then discharged into the duct through openings 66 and 66'. Bar 44 forms a partition in chamber 70 so that air from passages 64 and 64' must pass through holes 42 and 45 before reaching passages 66 and 66'. As the temperature of the air passing through the device varies, the center of thermostat 100 moves forwardly or rearwardly, depending on whether the temperature increases or decreases, and moves the shutters either to restrict ports 60 and 62 and opening 104, or to increase the capacity of ports 60 and 62 and restricting the capacity of port 104, thus regulating the amount of air bypassed through chamber 68 directly to the conduit or duct. When no odor neutralizing material is required or desired, hand 82 is moved to the off position, thereby closing ports 64 and 64' and 66 and 66' and turning off control switch 120, thus rendering the device inoperable.

While only one embodiment of the present odor control device has been described in detail herein, various changes and modifications may be made without departing from the scope of the invention.

I claim:
1. An odor control device for use with an air passage of a main system having a blower therein: comprising a body having a chamber, a panel secured to said body and having an air inlet port for admitting air to said chamber, a rotatable plate mounted on said panel, a container for odor conditioning material mounted over and rotatable with said rotatable plate, said panel and plate having a first pair of openings forming a variable air flow passage from said chamber to said container, and a second pair of openings forming a variable air flow passage from said container into the air passage of the system, the effective size of said first and second openings being varied by the rotation of said plate on said panel, a partition disposed between said first and second pairs of openings and between said plate and container for directing air flow into said container, and means for detachably securing said container over the first and second openings in said plate and panel.

2. An odor control device as defined in claim 1 in which an opening is provided in said body communicating directly with the passage of the main system and a thermostatically controlled valve controls the size of said opening.

3. An odor control device as defined in claim 1 in which a dial is provided between said panel and rotatable plate and said plate is rotated by the rotation of said container.

4. An odor control device as defined in claim 1 in which an opening connects said chamber with said main system and shutters control said opening and said air inlet port, and a thermostatic element connected to both of said shutters controls said shutters in response to variations in the temperature of the air passing through said chamber.

5. An odor control device as defined in claim 1 in which said container has a magnetic attractable, perforated plate across the opening thereof, and said means for detachably securing said container includes a bar magnet secured to said rotatable plate and forming said partition between said first and second pairs of openings so that the air passing through the device is directed through the perforated plate in said container where the air absorbs the odor neutralizing material.

6. An odor control device as defined in claim 5 in which an opening is provided in said body communicating directly with the passage of the main system and a thermostatically controlled valve controls the size of said opening.

7. An odor control device as defined in claim 5 in which a thermostatically controlled valve controls the flow of air through said air inlet port.

8. An odor control device as defined in claim 5 in which an opening connects said chamber with said main system and shutters control said opening and said air inlet port, and a thermostatic element connected to both of said shutters controls said shutters in response to variations in the temperature of the air passing through said chamber.

9. An odor control device as defined in claim 1 in which said dial has off and on positions and a switch connected to the controls of the main blower system may control said blower independently of the controls on the main system.

10. An odor control device as defined in claim 9 in which a means is attached to said rotatable plate for operating said switch.

11. An odor control device as defined in claim 10 which a means is provided for manually controlling said switch separately from said rotatable plate.

* * * * *